(12) United States Patent
Pinchuk

(10) Patent No.: US 6,929,659 B2
(45) Date of Patent: Aug. 16, 2005

(54) METHOD OF PREVENTING THE DISLODGMENT OF A STENT-GRAFT

(75) Inventor: Leonard Pinchuk, Miami, FL (US)

(73) Assignee: SciMed Life Systems, Inc., Maple Grove, MN (US)

(*) Notice: Subject to any disclaimer, the term of this patent is extended or adjusted under 35 U.S.C. 154(b) by 122 days.

(21) Appl. No.: 10/082,920

(22) Filed: Feb. 25, 2002

(65) Prior Publication Data

US 2002/0173836 A1 Nov. 21, 2002

Related U.S. Application Data

(63) Continuation-in-part of application No. 09/580,672, filed on May 30, 2000, now abandoned, which is a continuation of application No. 09/232,763, filed on Jan. 15, 1999, now abandoned, which is a continuation-in-part of application No. 09/134,887, filed on Aug. 14, 1998, now Pat. No. 6,348,066, which is a continuation of application No. 08/806,739, filed on Feb. 27, 1997, now abandoned, which is a continuation-in-part of application No. 08/554,694, filed on Nov. 7, 1995, now Pat. No. 5,628,788.

(51) Int. Cl.$^7$ .................................................. A61F 2/06
(52) U.S. Cl. ........................ 623/1.13; 623/1.23; 623/903
(58) Field of Search ............................... 623/1.13, 1.15, 623/1.23, 903

(56) References Cited

U.S. PATENT DOCUMENTS

| | | | |
|---|---|---|---|
| 3,105,492 A | 10/1963 | Jeckel | |
| 3,272,204 A | 9/1966 | Artandi | |
| 3,304,557 A | 2/1967 | Polansky | |
| 3,463,158 A | 8/1969 | Schmitt et al. | |
| 3,479,670 A | 11/1969 | Medell | |
| 3,878,565 A | 4/1975 | Sauvage | |
| 3,993,078 A | 11/1976 | Bergentz et al. | |
| 4,140,126 A | * | 2/1979 | Choudhury .................. 606/194 |
| 4,610,688 A | 9/1986 | Silvestrini et al. | |
| 4,655,771 A | 4/1987 | Wallsten | |
| 4,731,073 A | 3/1988 | Robinson | |
| 4,743,251 A | 5/1988 | Barra | |
| 4,954,126 A | 9/1990 | Wallsten | |
| 5,061,275 A | 10/1991 | Wallsten | |
| 5,064,435 A | 11/1991 | Porter | |
| 5,123,917 A | 6/1992 | Lee | |
| 5,234,457 A | 8/1993 | Andersen | |
| 5,330,500 A | 7/1994 | Song | |
| 5,383,926 A | 1/1995 | Lock et al. | |
| 5,405,378 A | 4/1995 | Strecker | |
| 5,443,499 A | * | 8/1995 | Schmitt ...................... 623/1.49 |
| 5,476,508 A | 12/1995 | Amstrup | |

(Continued)

FOREIGN PATENT DOCUMENTS

WO WO88/00813 2/1988

Primary Examiner—Paul B. Prebilic
(74) Attorney, Agent, or Firm—RatnerPrestia

(57) ABSTRACT

Endoluminal stent-grafts include several features which restrict dilation subsequent to installation but which allow the stent-grafts to be installed in the same manner as a conventional stent-graft. According to one embodiment, sutures are attached to an expanded stent-graft. The suture material is preferably braided PET or polypropylene and sutures are interwoven into the stent at substantially regular intervals. A second embodiment utilizes a band material in lieu of suture material. A third embodiment utilizes a warp knit tubular sheath with inlay yarn. The warp knit tubular sheath with inlay yarn may also act as the graft material. The invention includes a method of using these stent-grafts to prevent the dislodgment of an endoluminal stent-graft after deployment. The method includes the step of determining the maximum stent-graft diameter and related size of dilation restriction means to prevent excessive stent-graft shortening after initial deployment.

6 Claims, 7 Drawing Sheets

U.S. PATENT DOCUMENTS

| | | |
|---|---|---|
| 5,507,767 A | 4/1996 | Maeda et al. |
| 5,507,769 A | 4/1996 | Marin et al. |
| 5,534,007 A | 7/1996 | St. Germain et al. |
| 5,571,135 A | 11/1996 | Fraser |
| 5,752,522 A * | 5/1998 | Murphy ..................... 600/587 |
| 5,755,772 A * | 5/1998 | Evans et al. ................ 128/898 |
| 5,824,040 A * | 10/1998 | Cox et al. .................. 623/1.35 |
| RE35,988 E | 12/1998 | Winston et al. |
| 5,843,158 A | 12/1998 | Lenker |
| 5,849,037 A | 12/1998 | Frid |
| 6,273,895 B1 | 8/2001 | Pinchuk et al. |
| 6,348,066 B1 * | 2/2002 | Pinchuk et al. ............ 623/1.16 |

* cited by examiner

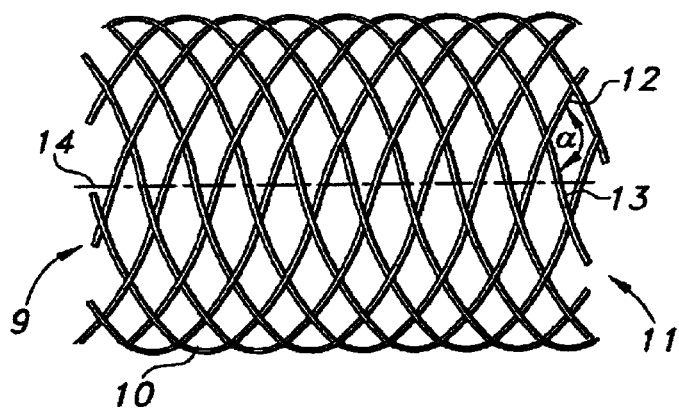
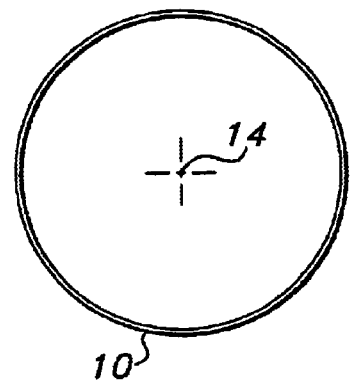
FIG. 1
(PRIOR ART)
FIG. 1A
(PRIOR ART)
(PRIOR ART)
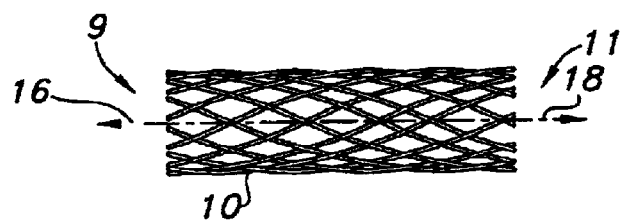
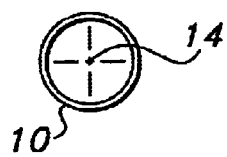
FIG. 2
(PRIOR ART)
FIG. 2A
(PRIOR ART)

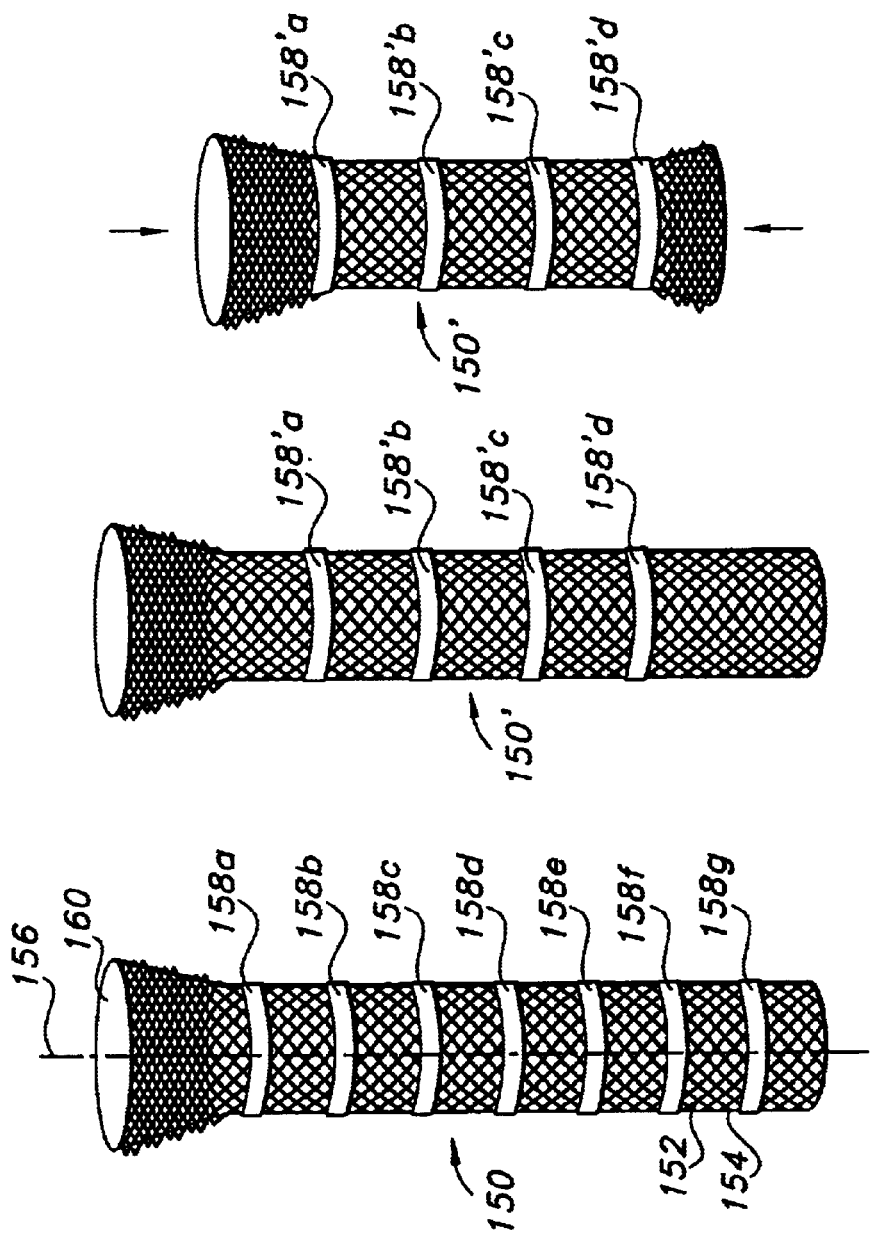

US 6,929,659 B2

METHOD OF PREVENTING THE DISLODGMENT OF A STENT-GRAFT

This application is a continuation-in-part of U.S. Ser. No. 09/580,672 filed May 30, 2000 which is a continuation of U.S. Ser. No. 09/232,763 filed Jan. 15, 1999 (abandoned), which is a continuation-in-part of U.S. Ser. No. 09/134,887 filed Aug. 14, 1998 (now U.S. Pat. No. 6,348,066), which in turn is a continuation of U.S. Ser. No. 08/806,739 filed Feb. 27, 1997 (abandoned), which was a continuation-in-part of U.S. Ser. No. 08/554,694 filed Nov. 7, 1995 (now U.S. Pat. No. 5,628,788).

BACKGROUND OF THE INVENTION

1. Field of the Invention

The invention relates to implantable prostheses. In particular, the invention relates to endoluminal stent-grafts which are deployed in blood vessels to bridge aneurysms. The invention is particularly related to a method for using stent-grafts which incorporate a structure for restricting dilation of the stent-graft after it is implanted.

2. State of the Art

Transluminal prostheses are well known in the medical arts for implantation in blood vessels, biliary ducts, or other similar organs of the living body. These prostheses are commonly known as stents and are used to maintain, open, or dilate tubular structures or to support tubular structures that are being anastomosed. When biocompatible materials are used as a covering or lining for the stent, the prosthesis is called a stent-graft. If used specifically in blood vessels, the stent-graft is known as an endovascular graft. A stent or stent-graft may be introduced into the body by stretching it longitudinally or compressing it radially, until its diameter is reduced sufficiently so that it can be fed into a catheter. The stent-graft is delivered through the catheter to the site of deployment. If the stent-graft is a self-expanding stent-graft, when it is released from the catheter, it self-expands. If the stent-graft is not self-expanding, upon release from the catheter it is mechanically expanded (e.g., by a balloon). Regardless of whether they are self-expanding or not, stent-grafts introduced in this manner are known as endoluminal stent-grants.

A typical state of the art self-expanding stent, such as disclosed in U.S. Pat. No. 4,655,771 to Wallsten or in U.K. Patent Number 1,205,743 to Didcott, is shown herein in prior art FIGS. 1, 1a, 2, and 2a. Didcott and Wallsten disclose a tubular body stent 10 composed of wire elements, e.g., 12, 13, each of which extends in a helical configuration with the centerline 14 of the stent 10 as a common axis. Half of the elements, e.g. 12, are wound in one direction while the other half, e.g. 13, are wound in an opposite direction. With this configuration, the diameter of the stent is changeable by axial movement of the ends 9, 11 of the stent. Typically, the crossing elements form a braid-like configuration and are arranged so that the diameter of the stent 10 is normally expanded as shown in FIGS. 1 and 1a. The diameter may be contracted by pulling the ends 9, 11 of the stent 10 away from each other as shown by arrows 16, 18 in FIG. 2. When the ends of the body are released, the diameter of the stent 10 self-expands and draws the ends 9, 11 of the stent closer to each other. The contraction to stretching ratio and radial pressure of stents can usually be determined from basic braid equations. A thorough technical discussion of braid equations and the mechanical properties of stents is found in Jedweb, M. R. and Clerc, C. O., "A Study of the Geometrical and Mechanical Properties of a Self-Expanding Metallic Stent—Theory and Experiment," *Journal of Applied Biomaterials*; Vol. 4, pp. 77–84 (1993). In general, however, the contraction to stretching ratio is related to the axially directed angle $\alpha$ between the crossing elements 12, 13 in the expanded state as shown in FIG. 1. As explained in Didcott, the greater the magnitude of the angle $\alpha$, the greater the amount of axial extension will be required to contract the diameter of the stent.

Prior art FIG. 3 shows a state of the art stent-graft 20 which includes a braided mesh stent exoskeleton 22 and an inner biocompatible liner 24. The stent shown is a Didcott-type stent with a crossing angle $\beta \approx 90°$, one straight 26 and one flared end 28. The liner (graft material) is polyethylene terepthalate (PET), polycarbonate urethane, or expanded polytetrafluroethylene (EPTFE) material which is attached to the stent by means of sutures or adhesives. However, those skilled in the art will appreciate that the state of the art stent-grafts include stents which are made of various different materials and which include self-expanding as well as balloon expandable stents. In addition, the graft materials of the state of the art stent-grafts include polyurethane, silicone rubber, polypropylene, polyolefin, collagen, elastin, etc. The graft material may be non-woven, woven, spun, knitted, braided, expanded, etc. It can be attached to the inside of an "exoskeleton" stent or to the outside of an "endoskeleton" stent by sutures, adhesives, co-braids, staples, etc.; or it can be attached within (i.e., both inside and outside) the skeleton if desired.

As shown in FIGS. 4–7, the exemplary stent-graft 20 of FIG. 3 is deployed with the aid of a catheter 30 and a guide wire 32. As shown in FIG. 4, the guide wire 32 is maneuvered through blood vessels to a location in artery 34 beyond aneurysms 36, 38. The stent graft (not shown in FIG. 4) is carried inside the catheter 30 which is guided over the guide wire (with the aid of fluoroscopy) to the site of the aneurysms 36, 38. The stent-graft is deployed as shown in FIGS. 5–7, by releasing one end 28 of the stent-graft 20 on one side of the aneurysms 36, 38. This is usually accomplished with the aid of a pusher (not shown) which moves inside the catheter and pushes the stent-graft out of the catheter as the catheter is pulled back. As the stent-graft 20 is released from the catheter 30, it expands as shown in the Figures and bridges the aneurysms 36, 38. Over time, i.e. several months, the porous liner 24 of the stent-graft 20 clots with blood and tissue ingrowth occurs. The liner thereby becomes non-porous or microporous allowing nutrient passage but no fluid leakage through the stent-graft into the aneurysms. It has been observed that, in many cases, after the graft has "healed-in," the stent-graft begins to dilate as shorten.

As illustrated in FIGS. 8–11, significant dilation of the stent-graft can result in a catastrophic failure. For example, FIG. 8 shows the stent-graft 20 installed in the abdominal aorta 40 bridging an aneurysm 42. During the first few months after implantation, the stent-graft 20 begins to heal-in. After six to twenty-four months, however, the stent-graft 20 may begin to dilate and shorten as shown in FIG. 9. This is particularly likely if the aneurysm 42 is empty rather than filled with organized clot. If unrestrained, the dilation of the stent-graft 20 will ultimately result in the end 26 of the stent-graft 20 slipping into the aneurysm 42 as shown in FIG. 10. This dislocation of the stent-graft can be catastrophic (even fatal) as it allows the aneurysm to be repressurized with blood, thereby risking rupture. While it is generally believed that a flared end of a stent-graft is more secure than a non-flared end, observations by the inventor suggest that this is not true. As shown in FIG. 11, the flared end 28 of the stent-graft 20 can become dislodged and slip into the aneurysm 42 with the same catastrophic results.

It is not entirely understood why stent-grafts dilate and become dislodged over time. It is believed that the dilation is the result of blood pressure acting on the wall of the stent-graft. At a low crossing angle of the stent wires, e.g., 90°, pressure inside the stent-graft will cause a dilation and shortening of the stent-graft. At a higher crossing angle of the stent wires, e.g., 120°, the pressure inside the stent-graft causes a lengthening of the stent-graft, which can result in a dislodging of the stent-graft. In this case, it is believed that the pulsing of blood pressure causes the stent-graft to alternately lengthen and shorten. This pulsing motion is believed to cause the stent-graft to "walk" along the arterial wall. Whatever mechanisms are involved, it is clear to the inventor that dilation of the installed stent-graft is a cause of stent-graft failure because of dislodgement.

SUMMARY OF THE INVENTION

It is therefore an object of the invention to provide an improved endoluminal stent-graft.

It is also an object of the invention to provide an endoluminal stent-graft which is resistant to dilation.

It is another object of the invention to provide an endoluminal stent-graft which is restricted from dilation beyond a selected point.

It is still another object of the invention to provide an endoluminal stent-graft which is resistant to dilation and which can be trimmed to length at the operating table.

Another object of the invention is to provide an endoluminal stent-graft which is resistant to dilation but which is still expandable during installation.

Still another object of the invention is to provide an endoluminal stent-graft which is resistant to dilation but which is still self-expanding during installation.

Still yet another object of the invention is to provide a method of preventing the dislodgement of a stent-graft after deployment.

In accord with these objects which will be discussed in detail below, the endoluminal stent-grafts of the present invention include several features which restrict dilation subsequent to installation but which allow the stent-grafts to be installed in the same manner as a conventional stent-graft. According to one embodiment, a suture or a plurality of sutures are attached to an expanded conventional stent-graft. Preferably, individual sutures are used to distribute the load of dilation restriction among many sutures and to allow the stent-graft to be trimmed to length at the operating table. The sutures can be placed on the outside or the inside of the stent-graft or sandwiched between the stent and the graft material. Various placement and attachment designs for the for the sutures are disclosed. The preferred embodiments include attaching the sutures to the outside of the stent-graft or intertwining the sutures with the wires of the stent. If the stent is a helically wound stent, it is preferred that the crossing angle of the wires be obtuse when the stent is fully expanded. According to a preferred embodiment, the crossing angle of the wires is between 100° and 120° when the stent is expanded. This crossing angle prevents the stent-graft from shortening when it is dilated. More particularly, an angle of approximately 109.5° is most preferred in order to maximum the volume in the braided suture and prevent expansion or contraction.

According to one preferred embodiment, the suture material is braided PET or polypropylene and sutures are interwoven into the stent at substantially regular intervals. The ends of each suture are preferably knotted together and then melt cut. The stent and suture assembly is then preferably spray coated with a melt adhesive, dried, and the graft liner is held against the melt adhesive while the assembly is heated to the melting point of the melt adhesive. The assembly is then cooled. Alternate embodiments include utilizing a band material in lieu of a suture material and utilizing a warp knit tubular sheath with inlay yarn in lieu of the sutures. According to one alternate embodiment, the warp knit tubular sheath with inlay yarn also acts as the graft material.

Additional objects and advantages of the invention will become apparent to those skilled in the art upon referent to the detailed description taken in conjunction with the provided figures.

DETAILED DESCRIPTION OF THE DRAWINGS

FIG. 1 is a broken side elevation view of a prior art braided stent expanded in a non-stressed position;

FIG. 1a is an end view of FIG. 1;

FIG. 2 is a broken side elevation view of a prior art stent of FIGS. 1 and 1a stretched and contracted;

FIG. 2a is an end view of FIG. 2;

FIG. 13 is a schematic perspective view of a second embodiment of a stent-graft according to the invention;

FIG. 14 is a schematic perspective view of an illustrative simplified version of the second embodiment of a stent-graft according to the invention;

FIG. 15 is a schematic perspective view of the stent-graft of FIG. 14 under axial compression;

The warp knit material used in the present invention is a more complex warp knit with an asymmetrical inlay thread. The material will stretch in one direction but is restricted by the inlay thread from stretching in another direction. The sleeve of the invention is manufactured with the material such that the stretchable axis is aligned with the longitudinal axis of the sleeve which is substantially collinear with the longitudinal axis of the stent-graft.

DETAILED DESCRIPTION OF THE PREFERRED EMBODIMENT

Figure 3:
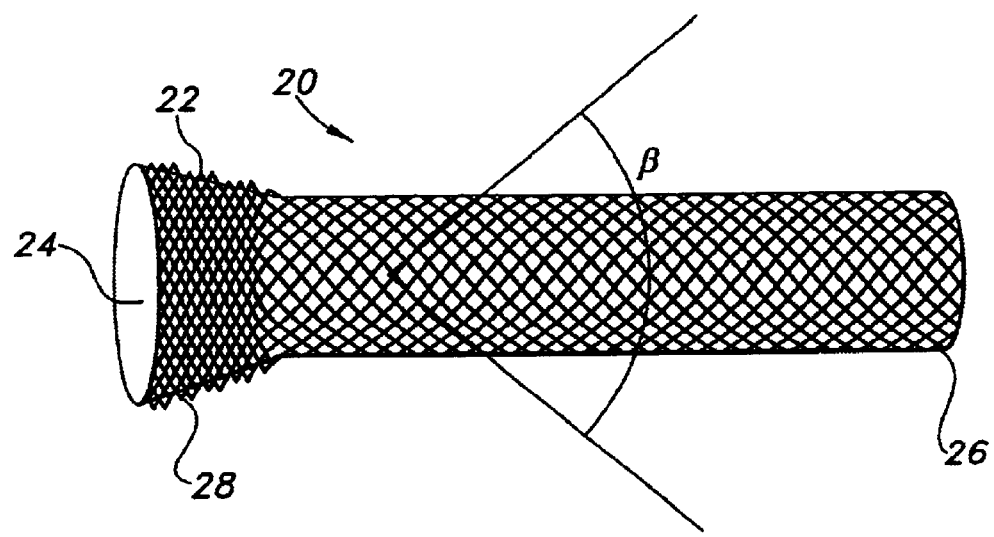
FIG. 3 is a schematic perspective view of a prior art stent graft.
Figure 4:
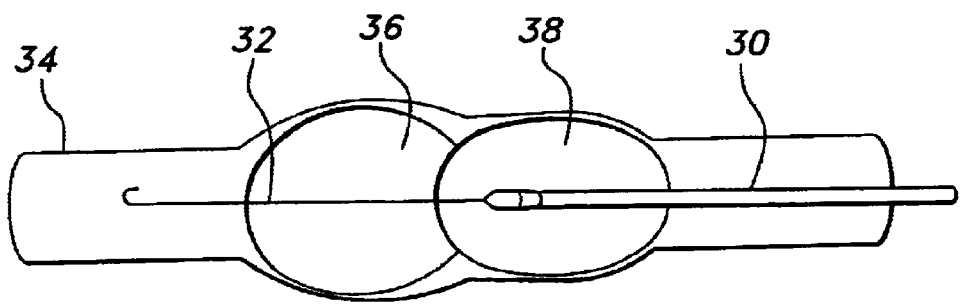
FIG. 4 is a schematic view of a prior art guide wire and deployment catheter near the site of an aneurysm.
Figure 5:
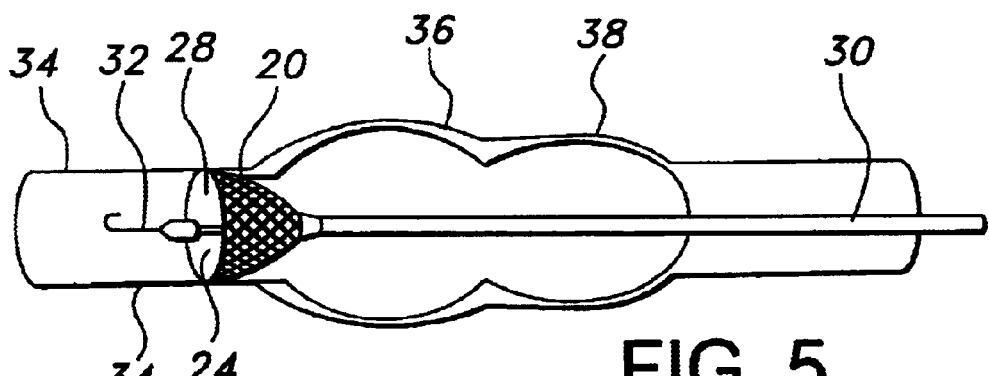
FIG. 5 is a view similar to FIG. 4 showing the prior art stent-graft in a first stage of deployment.
Figure 6:
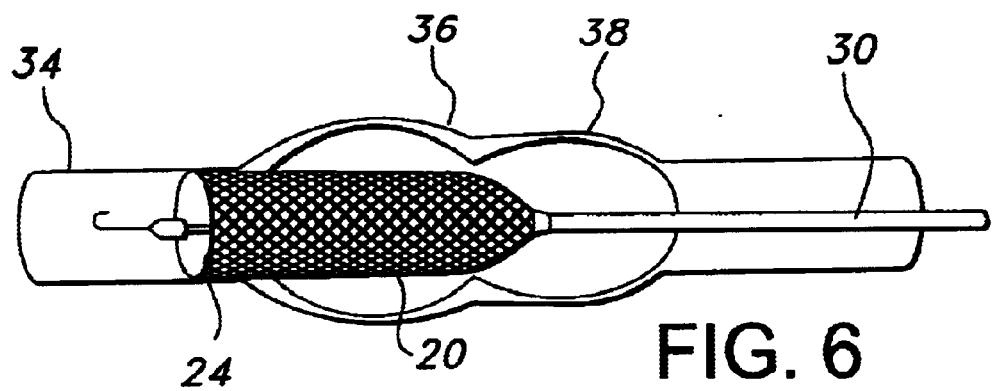
FIG. 6 is a view similar to FIG. 5 showing the prior art stent-graft in a second stage of deployment.
Figure 7:
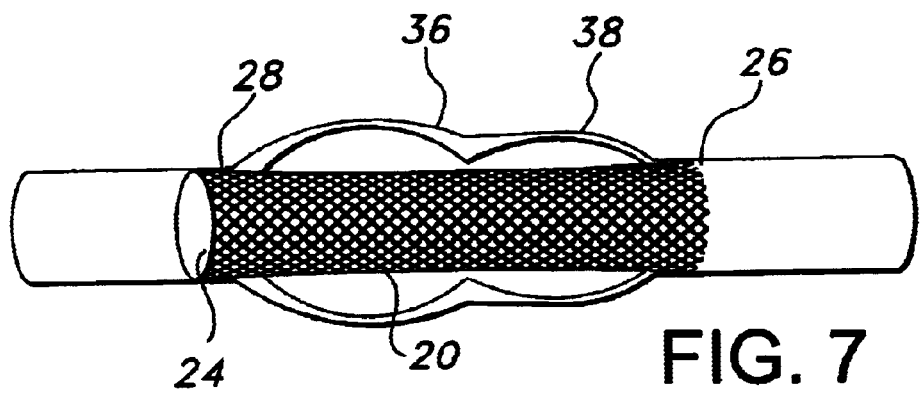
FIG. 7 is a view similar to FIG. 6 showing the prior art stent-graft deployed in an artery.
Figure 8:
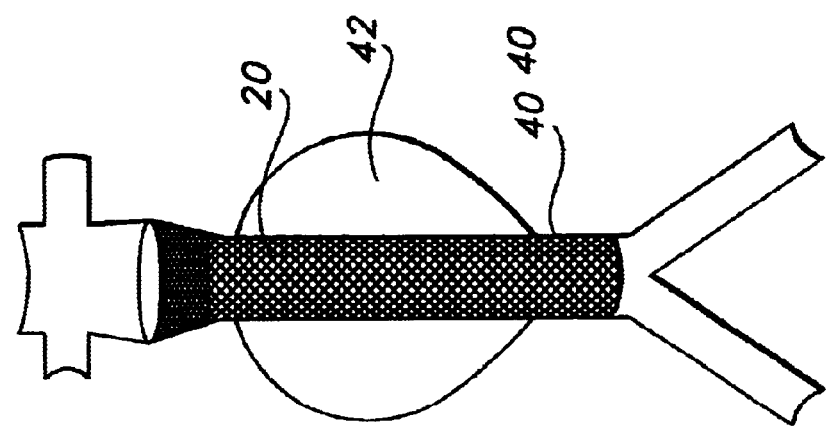
FIG. 8 is a schematic view of the prior art stent-graft deployed in the abdominal aorta.
Figure 9:
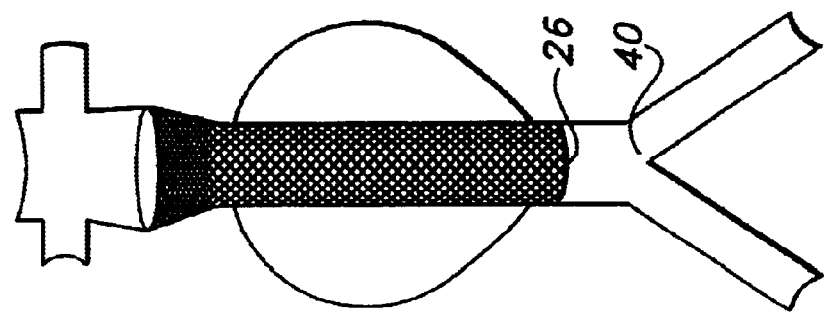
FIG. 9 is a view similar to FIG. 8 illustrating one end of the stent-graft partially dislodged.
Figure 10:
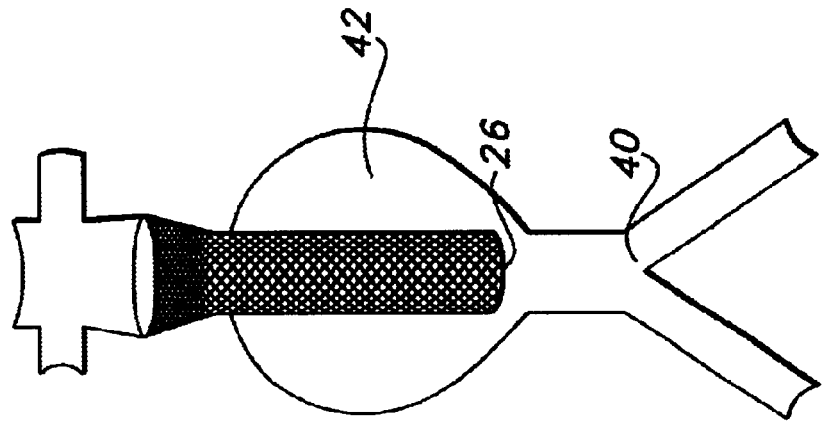
FIG. 10 is a view similar to FIG. 9 showing one end of the stent-graft completely dislodged.
Figure 12:
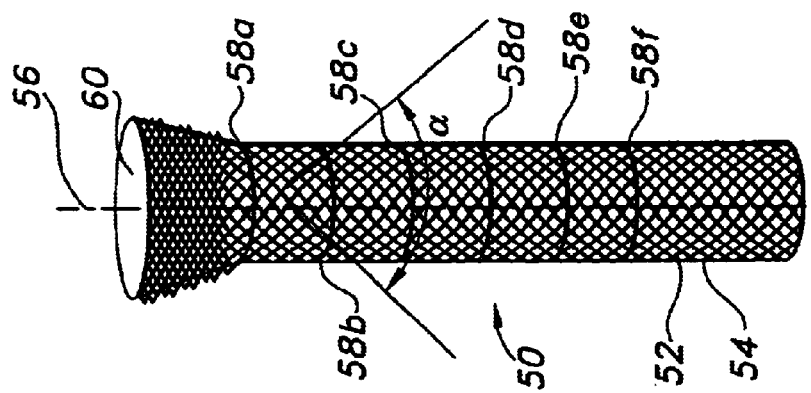
FIG. 12 is a schematic perspective view of a stent-graft according to the invention.
Figure 11:
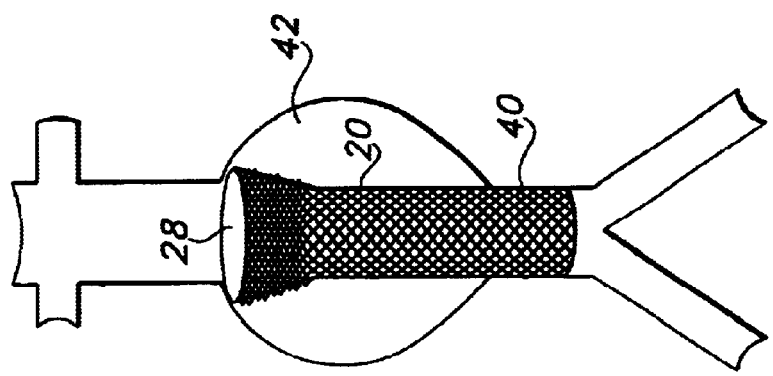
FIG. 11 is a view similar to FIGS. 8–10 showing the other end of the stent-graft completely dislodged.

Referring now to FIG. 12, a stent-graft 50 according to the invention includes a Walsten-type stent made up of wire elements, e.g. 52, 54, which are helically wound relative to the longitudinal axis 56 and braided relative to each other. The crossing angle Ø of the wires is preferably between approximately 100° and approximately 120°, and more preferably approximately 109.5° when the stent is in the expanded state. This angle is chosen so that if the stent is dilated beyond the expanded state it will not contract in length. According to the invention, a plurality of sutures, e.g. 58a–58f, are intertwined with the wires of the stent and spaced apart from each other as shown. According to one preferred embodiment, the suture material is braided PET or polypropylene, and sutures are interwoven into the stent at substantially regular intervals and in planes substantially perpendicular to the longitudinal axis of the stent. The ends of each suture are preferably knotted together and then melt cut. A conventional graft material 60 may be attached to the interior of the stent in a conventional way. However, according to a preferred embodiment, the stent and suture assembly is spray coated with a melt adhesive, dried, and the graft liner 60 is held against the melt adhesive while the assembly is heated to the melting point of the melt adhesive. The assembly is then cooled. The stent-graft may be deployed in a conventional manner and will exhibit significant resistance to dilation.

In lieu of a plurality of sutures, a single suture may be helically wound through the stent. A plurality of sutures is preferred because this allows the stent-graft to be trimmed to length at the operating table and because it spreads the load over many sutures. Although the preferred embodiment provides that the sutures be interwoven with the stent wires, the sutures may be attached to the stent in other ways such as crimping, gluing, melting, welding, or twisting. The sutures can be attached to themselves or to a strut or wire and may be placed on the inside or the outside of the stent. According to preferred embodiments, the sutures are sandwiched between the stent and the graft material. While the preferred suture material is braided PET or polypropylene, other suitable materials include NYLON, TEFLON, polyimide, stainless steel or tantalum. The suture material may be monofilament or braided. In addition, one or more sutures may be made of radiopaque material in order to locate the stent or a portion thereof; e.g., a bifurcated portion of the stent-graft. An important characteristic of the sutures is that they be flexible but substantially inelastic. Thus, sutures 58a–58f are preferably sized to be the size of the desired expanded diameter of the stent-graft 50. When the stent-graft is pulled down for insertion, the sutures will fold due to their flexibility; and when the stent-graft is released into its expanded state, the sutures will unfold to their maximum diameter. However, further dilation is resisted because the sutures are substantially inelastic.

Turning now to FIG. 13, a second embodiment of a stent-graft 150 according to the invention includes a Didcott-type stent made up of wire elements, e.g. 152,154, which are helically wound relative to the longitudinal axis 156 and braided relative to each other. The crossing angle of the wires is preferably between approximately 100° and approximately 120° when the stent is in the expanded state. A conventional graft material 160 may be attached to the interior of the stent in a conventional way. According to the invention, a plurality of bands, e.g. 158a–158f, are wrapped around the expanded stent and spaced apart from each other as shown. The bands which are preferably flat and wider than the sutures, can be braided, knitted, or woven and made of the same material as the sutures described above. The bands are attached to the inside or the outside of the stent by any of the methods described above, including sandwiching the bands between the stent and the graft material 160. The number and location of the bands may vary depending on the size and type of stent-graft. Preferably, the bands cover between 5% and 30% of the surface area of the stent.

FIGS. 14 and 15 illustrate a simplified example of the stent 150' having four centrally located bands 158'a–158'd. If a compressive force is applied to the ends of the stent as indicated by the arrows in FIG. 15, the bands will inhibit the stent from dilating.

A third embodiment of a stent-graft according to the invention includes a Didcott-type stent made up of wire elements which are helically wound relative to the longitudinal axis and braided relative to each other. The crossing angle of the wires is preferably between approximately 80° and approximately 100° when the stent is in the expanded state. A conventional graft material may be attached to the interior of the stent in a conventional way. According to the invention, a dilation restrictor sleeve is attached to the stent. The sleeve is made of a specially knit material and is attached to the sent in any of the manners described above with respect to sutures and bands. In order to appreciate the nature of the material used to fabricate the sleeve, it is useful to consider the nature of warp knit materials in general.

Figure 18:
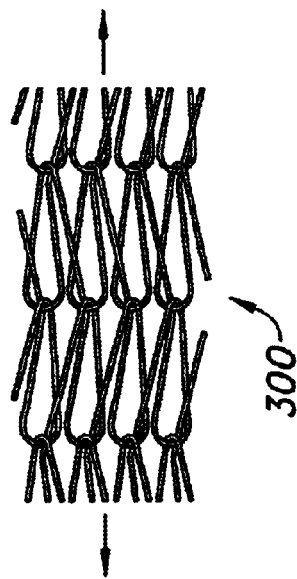
FIG. 18 is a view similar to FIG. 16 showing the fabric stretched in another direction.
Figure 17:
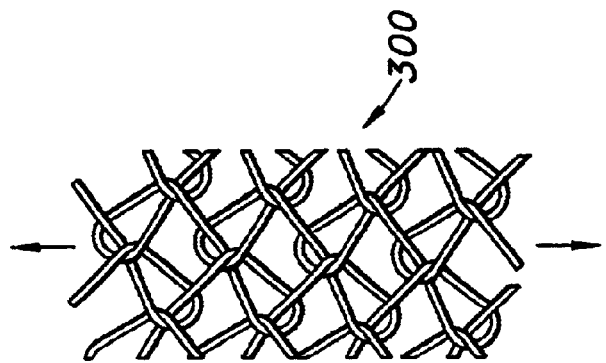
FIG. 17 is a view similar to FIG. 16 showing the fabric stretched in one direction.
Figure 16:
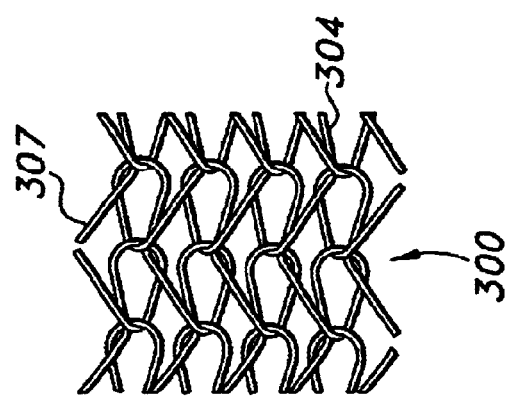
FIG. 16 is a schematic illustration of a prior art warp knit fabric.

Turning now to prior art FIGS. 16–18, a simple warp knit fabric 300 is made of symmetrically knitted threads 302 (shown in solid) and 304 (shown in outline). The symmetrical arrangement of the threads allows the fabric to stretch in two mutually orthogonal directions as shown in FIGS. 17 and 18.

The warp knit material used in the present invention is a more complex warp knit with an asymmetrical inlay thread. The material will stretch in one direction but is restricted by the inlay thread from stretching in another direction. The sleeve of the invention is manufactured with the material such that the stretchable axis is aligned with the longitudinal axis of the sleeve which is substantially collinear with the longitudinal axis of the stent-graft. Those skilled In the art will appreciate that the sleeve will allow the stent-graft to be easily "pulled down" for installation via a catheter and guide wire and will allow the stent-graft to expand to its determined diameter which restricts the stent-graft from dilation. In accord with the invention, the material used to make the sleeve may act as a substitute for the graft material. Those skilled In the art, with the benefit of the instant disclosure, will appreciate that the warp knit pattern can be used to knit a fabric which is suitable for use as a graft material.

The present invention is particularly useful in view of the recognized problem of the stents and stent-grafts moving, or migrating, over time after initial placement. Because of this potential for dilation and subsequent dislodgment, the present invention includes a method for preventing the dislodgment of an endoluminal stent graft after deployment into an aneurysm. The method includes the steps of determining the length of the aneurysm into which the stent-graft will be placed and the resultant length of the particular stent-graft needed to bridge it. Because the degree of linear shortening of a stent during radial dilation is dependent upon its particular architecture, the doctor would correlate the maximum allowable diameter of the stent with the minimum length of that particular stent needed to bridge the aneurysm.

Based on this maximum diameter calculation for the given stent, a stent-graft is selected having dilation restriction means which prevent excessive dilation which could lead to catastrophic shortening of the stent-graft over time after initial placement. That suitably sized and appropriately restricted stent-graft is then cut to length and deployed in the aneurysm.

A method of treating an aneurysm with a stent-graft can be performed which involves determining the length of the aneurysm, determining the diameter of the vessel into which the stent-graft will be placed, providing a stent-graft having a dilation restriction means for restricting dilation of the stent-graft beyond a maximum diameter where the maximum diameter is greater than the vessel diameter of the vessel, and trimming the stent-graft to a length that is greater than the length of the aneurysm when the stent-graft is dilated to its maximum diameter.

As discussed above, the dilation restriction means may compromise a suture material which may be flexible and inelastic. The stent-graft may be made of woven wires and have the suture material woven through the wires. The dilation restriction means may comprise a plurality of sutures spaced along the expandable stent-graft. The plurality of sutures may be located in a plurality of substantially parallel planes which are substantially perpendicular to a longitudinal axis of the stent-graft. In order to provide the suitably sized stent-graft after the minimum length is determined, the stent-graft may be cut just prior to deployment.

There have been described and illustrated herein several embodiments of endoluminal stent-grafts with dilation restriction and methods for their use. While particular embodiments of the invention have been described, it is not intended that the invention be limited thereto, as it is intended that the invention be as broad in scope as the art will allow and that the specification be read likewise. Thus, while particular Didcott-type stents have been disclosed, it will be appreciated that other types of stents, either self-expanded or balloon expandable, could be utilized. Also, while particular material have been disclosed for making the sutures, bands, and sleeves of the invention, it will be recognized that equivalent materials could be used with similar results obtained. Moreover, while a particular configuration has been disclosed in reference to the warp knit with inlay, it will be appreciated that other configurations could be used as well if they provide substantially the same results. Furthermore, while the invention has been disclosed in conjunction with a stent having one flared end and one non-flared end, it will be understood that he invention can be applied to stents having more than two ends (e.g., bifurcated stents) and to stents having any combination of flared and non-flared ends. It will therefore be appreciated by those skilled in the art that yet other modifications could be made to the provided invention without deviating from its spirit and scope as so claimed.

What is claimed:

1. A method of treating an aneurysm with a stent-graft comprising the steps of:
    (a) determining the length of the aneurysm;
    (b) determining the diameter of the vessel into which a stent-graft will be placed;
    (c) providing a stent-graft having dilation restriction means for restricting dilation of said stent-graft beyond a maximum diameter which maximum diameter is greater than the vessel diameter of step (b);
    (d) trimming the stent-graft to a length that is greater than the length of the aneurysm when the stent-graft is dilated to its maximum diameter.

2. The method of claim 1 wherein the dilation restriction means of the stent-graft provided in step (c) is comprised of suture material.

3. The method of claim 2 wherein said suture material is flexible and substantially inelastic.

4. The method of claim 1 wherein said stent-graft is made of woven wires and a suture material is woven through said wires.

5. The method of claim 1 wherein the dilation restriction means of the stent-graft provided in step (c) is comprised of a plurality of sutures spaced along said stent-graft.

6. The method of claim 1 wherein the dilation restriction means of the stent-graft provided in step (c) is comprised of a plurality of sutures located in a plurality of substantially parallel planes which are substantially perpendicular to a longitudinal axis of said stent-graft.

* * * * *